United States Patent [19]

Lifer et al.

[11] Patent Number: 5,312,936
[45] Date of Patent: May 17, 1994

[54] ANGIOTENSIN II ANTAGONISTS

[75] Inventors: Sherryl L. Lifer, Indianapolis; Winston S. Marshall, Bargersville; Fariborz Mohamadi; Jon K. Reel, both of Indianapolis; Richard L. Simon, Greenwood; Mitchell I. Steinberg; Celia A. Whitesitt, Greenwood, all of Ind.

[73] Assignee: Eli Lilly and Company, Indianapolis, Ind.

[21] Appl. No.: 761,127

[22] Filed: Sep. 17, 1991

Related U.S. Application Data

[62] Division of Ser. No. 444,456, Nov. 30, 1989, Pat. No. 5,073,566.

[51] Int. Cl.$^5$ .............. C07D 403/06; C07D 233/44; A61K 31/41; A61K 31/415
[52] U.S. Cl. ................. 548/253; 548/326.5; 548/330.1
[58] Field of Search ............ 514/381, 397, 399, 382; 548/253, 336, 337, 326.5, 311.5

[56] References Cited

U.S. PATENT DOCUMENTS 5,073,566 12/1991 Lifer .................... 514/381

FOREIGN PATENT DOCUMENTS 323841 7/1989 European Pat. Off. .

Primary Examiner—David B. Springer
Attorney, Agent, or Firm—Steven P. Caltrider; Leroy Whitaker; Robert A. Conrad

[57] ABSTRACT

This invention provides novel phenyl and heterocyclic derivatives, their pharmaceutical formulations and their use for antagonizing angiotensin II receptors in mammals.

10 Claims, No Drawings

ANGIOTENSIN II ANTAGONISTS

This application is a division of application Ser. No. 07/444,456, filed Nov. 30, 1989, now U.S. Pat. No. 5,073,566, issued Dec. 17, 1991.

BACKGROUND OF THE INVENTION

The hormone angiotensin II is recognized as the most potent vasopressor agent that produces hypertension in mammals. The action of the enzyme renin on the plasma protein substrate angiotensinogen results in the production of an inactive decapeptide, angiotensin I, which, upon conversion by the nonselective angiotensin converting enzyme (ACE) provides angiotensin II, the active hormone. See, e.g., Regoli et al., *Pharm. Rev.*, 26, 69 (1974). Angiotensin II causes vasoconstriction and stimulates aldosterone secretion (from the adrenal gland) which results in a rise of both blood volume and pressure. Angiotensin II also can act on other organs such as the brain (Fitzsimmons, *Rev. Physiol. Biochem. Pharmacol.*, 87, 117, (1980)), and a variety of glandular tissues including the kidney, liver and ovaries. Angiotensin II may also have a role in regulating the rate of cell growth and differentiation. See, e.g., Naftilan et al., *J. Clin. Invest.*, 83, 1419 (1989), and Jackson et al., *Nature*, 335, 437 (1988).

Some antihypertensive agents act as inhibitors of ACE thus blocking the formation of angiotensin II and its resulting increase of blood pressure. More recently, both peptide and non-peptide antagonists of angiotensin II have been disclosed—see, e.g., EPO Patent Application Publication 253310 and references contained therein, and Chill et al., *J. Pharmacol. Exp. Ther.*, 250, 867 (1989).

The present invention provides novel, potent, and effective compounds that antagonize angiotensin II at receptor sites in the body and are therefore useful as antihypertensive agents and for the treatment of congestive heart failure. (Douglas, W. W., in The Pharmacological Basis of Therapeutics, 7th Edition, Eds. A. G. Gilman, L. S. Goodman, T. W. Roll and F. Murod, MacMillan Publishing Co., New York, 1985) p. 652.

SUMMARY OF THE INVENTION

This invention provides compounds of Formula I

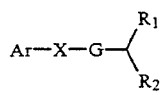

and pharmaceutically acceptable salts thereof where G is 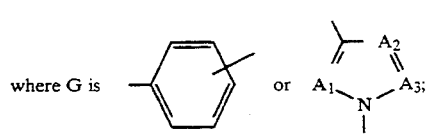

Ar is 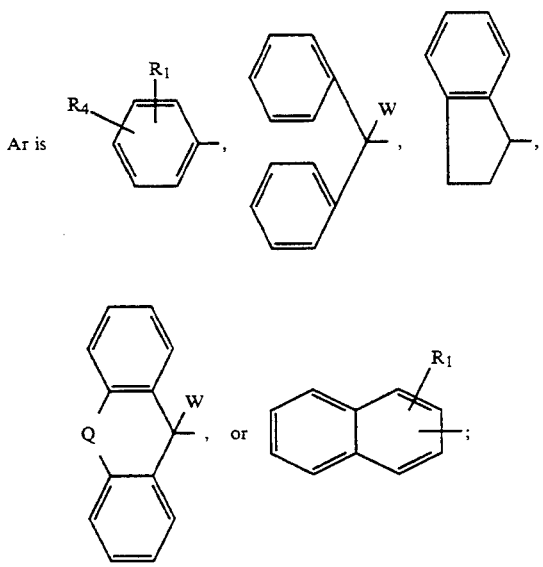

each of $A_1$, $A_2$, and $A_3$ is independently N or CH;

X is —CO—, —CONH—, —NHCO—, —CH$_2$CONH—, —O—, —NH—, —CH$_2$— or a bond;

each $R_1$ is independently —(CH$_2$)$_n$R$_3$;

$R_2$ is C$_4$–C$_7$ straight chain alkyl;

each $R_3$ is independently —OH, —COOH, or 5-tetrazolyl;

each n is independently 0, 1, 2, 3 or 4;

$R_4$ is H, OH, halo, nitro, methyl, amino, acetamido, or methanesulfonamido;

Q is a bond or —O—; and

W is H, methyl, ethyl, or hydroxy.

This invention also provides a method for treating hypertension which comprises administering to a mammal in need of such treatment an antihypertensive amount of a compound of Formula I.

Also provided are pharmaceutical formulations comprising a compound of Formula I together with one or more pharmaceutically acceptable excipients, carriers, or diluents therefor.

One further aspect of this invention is compounds which are intermediates for preparing the compounds of Formula I. These compounds are represented by Formula I'.

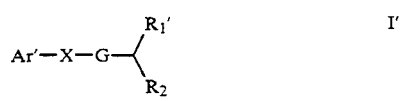

where G is 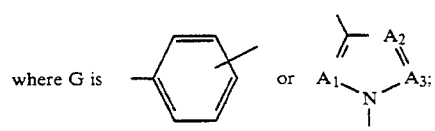

Ar' is

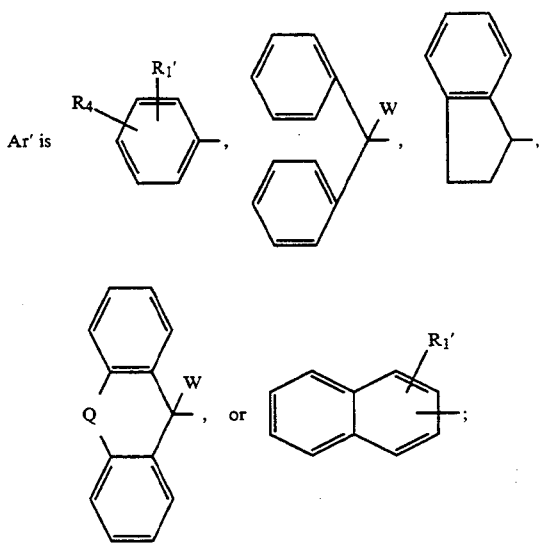

each of $A_1$, $A_2$, and $A_3$ is independently N or CH;
X is —CO—, —CONH—, —NHCO—, —CH$_2$CONH—, —O—, —NH—, —CH$_2$— or a bond;
each $R_1'$ is independently —(CH$_2$)$_n$R$_3'$;
$R_2$ is C$_4$–C$_7$ straight chain alkyl;
each $R_3'$ is independently —OH, —COOH, 5-tetrazolyl, —COO(C$_1$–C$_4$ alkyl), or —CN;
each n is independently 0, 1, 2, 3, or 4;
$R_4$ is H, OH, halo, nitro, methyl, amino, acetamido, or methanesulfonamido;
Q is a bond or —O—; and
W is H, methyl, ethyl, or hydroxy; provided at least one $R_3'$ is —COO(C$_1$–C$_4$ alkyl) or —CN.

DETAILED DESCRIPTION AND PREFERRED EMBODIMENT

Preferred compounds of this invention are those of Formula I wherein G is either phenylene or imidazolenyl, Ar is R$_3$-substituted phenyl optionally substituted with hydroxy, X is —CONH—, n is 0, and R$_2$ is n-hexyl. Particularly preferred compounds are those of Formula Ia:

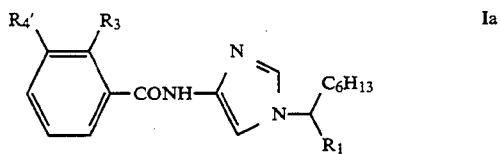

wherein R$_4'$ is hydrogen or hydroxy. Most preferred compounds are those wherein n is 0 and each R$_3$ is independently —COOH or 5-tetrazolyl.

As used in this document, the term "C$_1$–C$_4$ alkyl" includes methyl, ethyl, propyl, isopropyl, n-butyl, sec-butyl, iso-butyl, and tert-butyl. The term "C$_4$–C$_7$ straight chain alkyl" includes n-butyl, n-pentyl, n-hexyl, and n-heptyl. The term "halo" includes fluoro, chloro, bromo, and iodo.

In the definition of Formulas I and I', the G heterocyclic functionality is attached to X at the carbon atom between atoms A$_1$ and A$_2$. Thus, the —CHR$_1$R$_2$ substituent is attached to the nitrogen atom.

Similarly, while both the "normal" and "reverse" amides of linking group X are contemplated, only those acetamido functionalities wherein AR-X-G is Ar-CH$_2$CONH-G are contemplated.

By virtue of their acidic carboxylic acid or tetrazole moieties, the compounds of Formula I include the pharmaceutically acceptable base addition salts thereof. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine, and the like. The potassium and sodium salt forms are particularly preferred.

The compounds of Formula I where G is a heterocycle can also exist as pharmaceutically acceptable acid addition salts. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, xylenesulfonate, phenylacetate, phenylpropionate, phenylbutyrate, citrate, lactate, hippurate, $\beta$-hydroxybutyrate, glycolate, maleate, tartrate, methanesulfonate, propanesulfonate, naphthalene-1-sulfonate, naphthalene-2-sulfonate, mandelate and the like salts. The hydrochloride salt form is particularly preferred.

The pharmaceutically acceptable salts of compounds of Formula I can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of Formula I and I' exist, for example, the chiral carbon atom to which G, R$_1$ or R$_1'$, and R$_2$ are attached. This invention is not limited to any particular stereoisomer but includes all possible individual isomers and mixtures thereof.

The compounds of Formula I are prepared by standard methods from intermediates I'. Those compounds of Formula I' wherein one or more of R$_3'$ is cyano can be converted either to the 5-tetrazolyl final product (R$_3$ is 5-tetrazolyl) or the carboxylic acid final products (or the salts thereof) by methods known in the art. Thus, the cyano intermediates are treated with an alkali metal azide such as sodium azide, ammonium chloride or triethylamine hydrochloride, and (optionally) lithium chloride in a non-reactive high boiling solvent such as N,N-dimethylformamide (DMF), preferably at temperature from about 60°–125° C. Alternatively, tri-(n- butyl)tin azide or tetramethylguanadinium azide, in a solvent such as tetrahydrofuran, dimethoxyethane, diethoxyethane, or the like, may be used in place of the alkali metal azide, ammonium chloride, lithium chloride, and DMF.

The carboxylic acids of Formula I can be prepared by hydrolysis of either the cyano or ester intermediates of Formula I'. The hydrolysis generally involves the heating of the cyano derivative in aqueous alcohol in the presence of a base such a sodium or potassium hydroxide. When the ester intermediate is employed, it is treated with aqueous sodium or potassium hydroxide solution optionally in the presence of an alcohol preferrably at a temperature from approximately 50° C. up to the reflux temperature of the mixture. The free acid final product can be isolated by acidifying (for example, with 5N hydrochloric) the cooled reaction mixture. The salts of the carboxylic acid and tetrazole final products are made by reacting the free acid or tetrazole with the appropriate base by standard procedures.

The desired products from the above reactions can be isolated by conventional means, and preferably by chromatography. Column chromatography is a preferred method and high pressure column chromatography over silica gel offers a most efficient way of purifying the final products. Alternatively, crystallization of the acid, tetrazole, or salts may be employed to purify the desired final product.

One process for preparing the heterocyclic intermediates of Formula I' involves the alkylation of intermediate II with an alkylating reagent III to prepare intermediate IV as summarized by Scheme 1

Scheme 1

Ar'—X—G'—H + L—CHR$_1$R$_2$ ⟶ Ar'—X—G'—CHR$_1$R$_2$
II                III                        IV where Ar', X, R$_1$' and R$_2$ are the same as previously defined, G' is

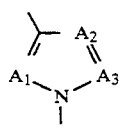

and L is a good leaving group such as chloro, bromo, iodo, mesyl, tosyl, and the like. This reaction usually involves approximately equimolar amounts of the two reagents, although other ratios, especially those wherein the alkylating reagent is in excess, are operative. The reaction is best carried out in a polar aprotic solvent employing an alkali metal salt or other such alkylation conditions as are appreciated in the art. When the leaving group is bromo or chloro, a catalytic amount of an iodide salt, such as potassium iodide, may be added to speed the reaction. Preferred reaction conditions include the following: lithium bromide and dimethylformamide, potassium fluoride on alumina, sodium bicarbonate in dimethylformamide, sodium hydride in dimethylformamide, potassium carbonate, potassium iodide, and either methylethyl ketone or acetone. The temperature of the reaction is preferably from about ambient temperature to about the reflux temperature of the reaction mixture. When elevated temperatures are employed, the reaction is generally complete in 1–4 hours.

The two carboxamide-type compounds of this invention can be prepared according to Scheme 2

Scheme 2

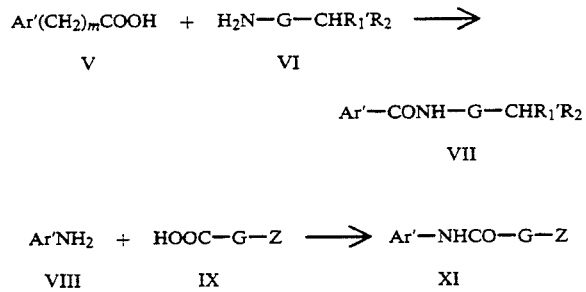

where Ar' and G are the same as previously described, m is 0 or 1, and Z is either hydrogen or —CHR$_1$'R$_2$'.

The transformation as depicted in Scheme 2 above can be accomplished by any of several known methods of coupling carboxylic acids to amines. For example, carboxylic acid V or IX can be transformed into a corresponding acid halide, particularly an acid chloride, and then reacted with the appropriate amine to provide amides VII or XI. Conversion of the acid to the corresponding acid chloride, for example, can be accomplished upon treatment with a reagent such as thionyl chloride or oxalyl chloride optionally in the presence of a nonreactive base and optionally in the presence of a aprotic nonreactive solvent. Preferred combinations include thionyl chloride treatment followed by reaction of the amine in potassium carbonate in tetrahydrofuran, or reaction of oxalyl chloride with the carboxylic acid followed by addition of the amine in dimethylformamide and triethylamine. Alternatively, the oxalyl chloride reaction can be performed in the presence of sodium hydride in tetrahydrofuran. The amine can also be introduced as an acid salt and added together with a nonreactive base. Thus, the amine hydrochloride may be added with triethylamine, pyridine, or the like.

Alternatively, other amide-condensing reagents may also be employed, such as 1,1'-carbonyldiimidazole or 1,3-dicyclohexylcarbodiimide. These reagents are usually employed in a nonreactive high boiling solvent such as dimethylformamide and optionally in the presence of reagents such as diisopropylethylamine, hydroxybenzotriazole, and the like in order to facilitate reaction.

Ketone-containing compounds of Formula I and I' can be prepared by reacting either an anhydride of Formula XII or carboxylic acid of Formula V with a compound of Formula XIII to provide the corresponding ketones XIV and XV, respectively.

Scheme 3

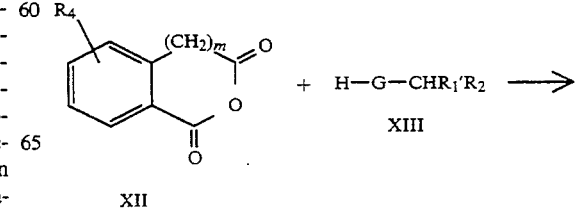

-continued
Scheme 3

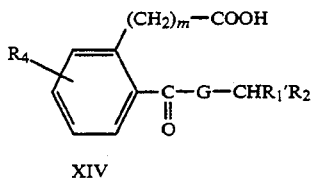

XIV

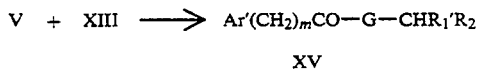

XV

As indicated in Scheme 3 above, the anhydride method is particularly preferred for preparing the preferred compounds of Formula Ia whereas the use of acids such as Formula V can more generally be employed.

In Scheme 3 above, $R_4$, G, Z, m, and Ar' are the same as previously defined.

The reactions protrayed in Scheme 3 are generally known as Friedel-Crafts reactions which involve reacting approximately equimolar amounts of the acid or anhydride with reagent XIII in the presence of a Lewis acid, such as aluminum chloride, in a non-reactive polar solvent such as dimethylformamide.

In a manner analogous to Scheme 3 above, preferred amide-containing compounds of Formula I or I' can be prepared according to the following Scheme:

Scheme 4

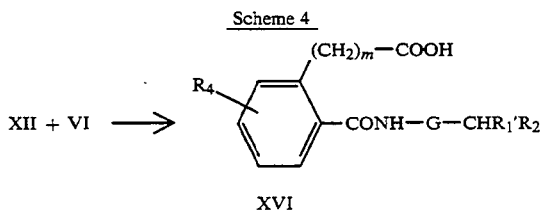

XVI

According to Scheme 4, the reaction of the appropriate anhydride XII and amine VI is accomplished by mixing the two reagents in one or more nonreactive solvents, such as dimethylformamide, ethanol, mixtures of the same, etc. This reaction therefore gives products similar to those found in Scheme 2 above which are, in part, the preferred compounds of Formula Ia. Alternatively, anhydride XII can be reacted with one equivalent of an alcohol to provide a monoacid monoester of Formula V which is reacted in accordance with Scheme 2.

Another method of preparing compounds of this invention include those of Scheme 5.

Scheme 5

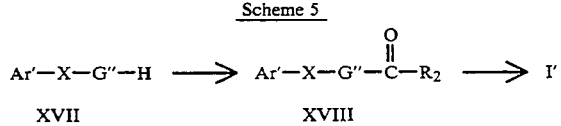

XVII     XVIII where G" is phenylene. In this sequence, intermediate XVII is acylated with an acid halide of the Formula $R_2COCl$. This reaction is a Friedel-Crafts reaction which is best carried out in the presence of a Lewis acid, such as aluminium chloride, in a nonreactive solvent such as dichloromethane. The resulting ketone intermediate XVIII can then be reacted with iodine and the appropriate alkylating agent, such as trimethyl orthoformate, to introduce the $R_1'$ functionality to prepare those compounds wherein n is 0. Alternatively, for compounds wherein n is 1–4, ketone intermediate XVIII can be reacted with a Wittig reagent such as those of the general formula $(CH_3O)_2PO(CH_2)_{n-1}COO(C_1-C_4\ alkyl)$ or $(CH_3O)_2PO(CH_2)_{n-1}CN$ to provide the corresponding ethylene derivative which can be transformed into the alkanoic ester or alkanenitrile upon reduction of the double bond. This reaction sequence is particularly useful in preparing compounds wherein G is phenylene and X is —O— or —CH$_2$—. When X is —CH$_2$— and G is a hetero group, other reaction schemes such as Scheme 1, may be employed.

When G is G", the ketone-containing compounds can be prepared by reacting an intermediate such as Br-G"-Z with a lithiating reagent, such as n-butyllithium, to produce the corresponding Li-G"-Z intermediate which can be reacted with the corresponding aldehyde AR'—CHO to provide the desired intermediate XVII where X is —CO—.

The directly substituted compounds of this invention, i.e., compounds wherein X is a bond, can be prepared in a variety of ways. When G is G", the compounds are best prepared according to the procedure of Scheme V. In the case of biphenyl compounds, reaction of the ketone with iodine and trimethylorthoformate does not introduce the desired functionality. Thus, in this case, the appropriate procedure either involves the Wittig reaction described above, or, when n is 0, the ketone may be reduced to the corresponding alcohol, for example, with sodium borohydride in the presence of ethanol, and the resulting alcohol intermediate transformed into the bromo derivative, upon treatment with phosphorus tribromide in a solvent such as dichloromethane. The bromo group is displaced upon treatment with cyanide, such as the treatment with sodium or potassium cyanide, upon heating in a solvent such as dimethylsulfoxide. The nitrile group can then be transformed into the corresponding tetrazole or hydrolyzed to the acid as described above.

The heterocyclic compounds of this invention (G=G', X=a bond) are best prepared by reacting the same dilithium hetero intermediate as described above with the appropriate derivative Ar'-Br to provide the corresponding intermediate compound II which can then be transformed in the usual manner.

As noted above, the compounds of this invention contain at least one chiral center, that being the carbon atom to the G, $R_1$, and $R_2$ substituents. While all of the above schemes address reactions involving racemic reagents and products, each of the reactions can be performed using a chiral starting material to provide a particular enantiomer of interest. The reaction of Scheme 1 is particularly useful since introduction of the chiral center is the penultimate step. Alternatively, particular isomers can be isolated from the racemate by resolution employing standard methods, such as fractional crystallization, high pressure liquid chromatography, and the like. These resolutions can be accomplished either on the final product I, intermediate I', at any stage along the synthetic pathway, or on derivatives of the final products and intermediates.

Compound of Formula I and I' wherein the Ar group contains an active methylene on the α-carbon to the carbonyl, such as Ar=(C$_6$H$_5$)$_2$CH—, can be converted to the corresponding hydroxy derivative (e.g., C$_6$H$_5$)$_2$C(OH)— upon base hydrolysis. This transformation can usually be accomplished upon hydrolysis of an ester group of such intermediates. Thus, the preparation of such compounds wherein W hydroxy can generally be accomplished in this manner.

The introduction of methyl or ethyl substituents in such compounds can be accomplished by the applicable reactions above employing starting materials wherein Ar' has the appropriate W substituent.

In all the above schemes, it is preferred that the reactions be carried out wherein all of the $R_3'$ groups are either ester or nitrile which can then be transformed as described above. However, as will be appreciated by one skilled in the art, many of these reactions can be performed on the free acid or tetrazole if the appropriate reaction conditions, blocking reagents, or the like are used. Since the nitrile and ester groups are considerably different in their sensitivity to hydrolysis, the sequence for transforming intermediates of Formula I' to final products having both an acid and a tetrazole group is not critical. However, preferrably a nitrile group is transformed into a corresponding tetrazole before hydrolysis of an ester.

Intermediates II, III, V, VI, VIII, IX, XII, XIII, and XVII, and any other reagents required for their transformation, are either commercially available, known in the art, or can be prepared by methods known in the art. In particular, intermediates such as those of Formula VI and VIII can be prepared from the corresponding nitro compound preferrably by hydrogenation and are generally used immediately without further isolation. Such a transformation is best accomplished in the presence of a catalyst, such a palladium on carbon, in an inert solvent such as ethanol.

The nitro precursors to compounds VI and VIII can be prepared in one of at least two ways. Either the corresponding aryl nucleus can be nitrated under standard nitrating conditions, or the nitro compound can be first modified, such as introducing the $R_4$ substituent in the phenyl ring or alkylation of the G ring with intermediate III. Alternatively, the —$CHR_1'R_2$ sidechain can be built up sequentially, such as through the standard alkylation of the basic intermediate, such as, for example, phenyl acetate to provide the α-alkylphenyl acetate which can then be nitrated, reduced, etc.

The amino-containing compounds ($R_4$ is amino, acetamido, or methanesulfonamido) can be either prepared directly by the methods described above or prepared from the corresponding nitro or amino compounds of Formulas I or I'. For example, 3-nitrophthalic acid anhydride can be hydrogenated to prepare the corresponding 3-aminophthalic anhydride intermediate. The treatment of this amino compound with acetyl chloride in potassium carbonate and 2-butanone provides the corresponding 3-acetamidophthalic anhydride intermediate. In contrast, treatment of the aminophthalic anhydride with methanesulfonyl chloride and methane sulfonic anhydride at 100° C. provides the corresponding 3-methanesulfonamidophthalic anhydride intermediate. Any of these anhydrides can then be employed in the corresponding transformations as described above. Alternatively, the nitro intermediate of Formula I' can be similarly hydrogenated, sulfonylated, or acylated to provide the corresponding amino, sulfonamido, or acetamido intermediates of Formula I'.

The introduction of the various —$(CH_2)_nR_3'$ functionalities can be introduced either directly or through the manipulation of precursors to that side chain. For example, an intermediate, such as a nitro precursor to compound VI, where $R_1'$ is —COO($C_1$-$C_4$ alkyl), can be reduced to the corresponding aldehyde or otherwise transformed to a compound corresponding to that of VI wherein $R_1'$ is —CHO. The aldehyde can then be reacted with the appropriate Wittig reagent to introduce the appropriate number of carbon atoms and the carboxylic acid ester or nitrile functionality with the $R_1'$ chain being unsaturated. Catalytic reduction can then be employed to provide the corresponding alkanoic ester or alkylnitrile.

In some cases where G is the nitrogen heterocycle (G'), an intermediate corresponding to Formula II can be alkylated in the same manner as provided in Scheme 1. Thus, when G is G', intermediates VII, XI, XIV, XV and XVI can usually be transformed from compounds wherein Z is hydrogen to the corresponding compounds wherein Z is —$CHR_1'R_2$ according to the process of Scheme 1. However, in those cases where the amino heterocycle is unstable, preparing intermediate II must be accomplished by alternate means. For example, if X is —CONH— and G' is 4-imidazolyl, compound II cannot be prepared by reacting V with 4-aminoimidazole since the latter is not stable.

In the reactions preparing compounds VII and XVI where there is a carboxylic acid functionality attached directly or through a methylene group to the ortho position of the phenyl ring of the Ar' group, reaction of either the acid or anhydride with amine VI may result in either the amide VII or XVI as drawn, or may result in a ring closed phthalimide or homophthalimide intermediate which will, upon hydrolysis, ring open to the ortho-carboxylic or -acetic acid final product.

The amine containing compounds of this invention (X=—NH—) can be prepared in at least two ways. When G is phenylene, an Ullmann reaction can be performed on an intermediate of Formula VIII and a bromo containing compound of the Formula Br—G'-'—$COR_2$ to provide compounds of Formula XVIII wherein X is —NH—. Typical Ullmann conditions include the reaction of these reagents in the presence of copper bronze and copper chloride in the presence of pyridine or dimethylformamide. For preparing the heterocyclic compounds of this invention, a similar reaction can be employed. In this way, intermediate VIII is reacted with a compound of the formula BR-G'-D where D is a protecting group such as a benzyl functionality. Again under Ullmann conditions, the resulting product is a protected form of Compound II which can then be deblocked (i.e., debenzylated) and alkylated in the usual manner. These same schemes can be used to make the ethers (X=—O—) of this invention beginning with the hydroxy analog to compound VIII.

The following Examples and preparations are provided merely to further illustrate the invention. The scope of the invention is not construed as merely consisting of the following Examples.

In the following Examples and preparations, melting point, nuclear magnetic resonance spectra, mass spectra, high pressure liquid chromatography over silica gel, and N,N-dimethylformamide are abbreviated m.p., NMR, MS, HPLC, and DMF, respectively. The reported melting points are uncorrected. The terms "NMR" and "MS" indicate that the spectrum was consistent with the desired structure.

PREPARATION 1

4-Nitro-α-hexyl-1H-imidazole-1-acetic acid ethyl ester

Sixty percent sodium hydride in oil (14.8 g) was washed with hexane to remove the oil and the residue covered with DMF. A solution of 41.8 g of 4-nitroimidazole was added as a solution in DMF to the sodium hydride mixture. After addition, the mixture was heated at reflux for one hour, cooled, at a solution of 92 g of ethyl 2-bromooctanoate in DMF was added. The mixture was heated at reflux for two hours, allowed to cool, and stirred overnight at room temperature. The mixture was added to ice water, extracted with ethyl acetate, and the combined organic extracts washed with water, dried over sodium sulfate, and concentrated in vacuo to provide 104.0 g of the desired titled intermediate, oil.

Analysis for $C_{13}H_{21}H_3O_4$: Calc.: C, 55.11; H, 7.47; N, 14.83; Found: C, 54.89; H, 7.62; N, 14.95.

Prepared in the same manner was 4-nitro-α-hexyl-1H-imidazole-1-acetonitrile.

Analysis for $C_{10}H_{16}H_4O_2$: Calc.: C, 55.92; H, 6.83; N, 23.71; Found: C, 55.64; H, 6.72; N, 23.98.

PREPARATION 2

4-Nitro-β-hexyl-1H-imidazole-1-propanoic acid methyl ester

The title intermediate was prepared by combining 5.0 grams of 4-nitroimidazole, 8.26 g of methyl 2-nonenate, 4.08 g of sodium bicarbonate, and 200 ml of dimethylformamide and heating the mixture at 80° C. for 18 hours. After cooling, the mixture was poured into water and extracted into ethyl acetate. The organic layer was concentrated in vacuo and the residue purified by HPLC over a silica column eluting with ethyl acetate. The appropriate fractions were combined and concentrated in vacuo to provide 2.2 g of the desired titled intermediate.

Analysis for $C_{13}H_{21}N_3O_4$: Calc.: C, 55.11; H, 7.47; N, 14.83; Found: C, 55.37; H, 7.37; N, 14.58.

PREPARATION 3

4-Nitro-β-hexyl-1H-imidazole-2-ethanol

To 5 g of 4-nitro-α-hexyl-1H-imidazole-1-acetic acid ethyl ester in 100 ml of dry methanol were added 2 molar equivalents of lithium borohydride dropwise as a solution in 70 ml of methanol. The reaction was allowed to stir at room temperature for 6 hours. The solvent was removed in vacuo to provide a white solid which was slurried in diethyl ether and filtered to provide 2.3 g of the desired titled intermediate, m.p. 83°-84° C.

Analysis for $C_{11}H_{19}N_3O_3$; Calc.: C, 54.76; H, 7.94; N, 17.42; Found: C, 54.50; H, 7.71; N, 17.36.

PREPARATION 4

4-Nitro-α-hexyl-1H-imidazole-1-acetaldehyde

To 1.3 ml of oxalyl chloride in 32 ml of dry methylene chloride previously cooled to −55° to −60° C. were added 2.2 ml of dimethylsulfoxide dropwise while maintaining the temperature at −55° to −60° C. After stirring for 2 minutes, 3 g of the alcohol from Preparation 3 above were added as a solution in 20 ml of methylene chloride dropwise over a 5 minute period. After stirring for 15 minutes, 9.2 ml of triethylamine was added dropwise while maintaining the temperature. The reaction mixture was then allowed to warm to room temperature and was quenched with water. The mixture was extracted with methylene chloride and the organic layer dried over sodium sulfate and concentrated in vacuo. The residue was purified by HPLC eluting with 1:1 ethyl acetate/hexane. The appropriate fractions were combined and concentrated to provide 800 mg of the title intermediate used directly into next reaction.

PREPARATION 5

4-Nitro-γ-hexyl-1H-imidazole-1-but-2-enoic acid methyl ester

To 800 mg of trimethyl phosphonoacetate in 50 ml of tetrahydrofuran cooled to 0° C. were added 2.8 ml of 1.6M butyllithium in hexane while maintaining the temperature in 0° C. After stirring for 5 minutes, the mixture was allowed to warm to room temperature. After once again cooling to 0° C., 700 mg of the aldehyde from Preparation 4 above were added dropwise as a solution in 50 ml of tetrahydrofuran. The mixture was allowed to warm to room temperature and stirred for 2 hours. After cooling, the reaction was quenched with water and the reaction extracted into ethyl acetate. The organic layer was dried over sodium sulfate, concentrated in vacuo, and the residue purified by HPLC eluting with diethyl ether to provide 500 mg of the desired title intermediate. MS: $M^+=295$.

PREPARATION 6

Ethyl α-hexylphenyl acetate

Fifty milliliters of ethyl phenylacetate were dissolved in 600 ml of tetrahydrofuran and cooled to −20° C. Over a period of 15 minutes, 13.9 g of 60% sodium hydride in oil were added in portions. To the mixture were added 60 ml of 1-bromohexane over a 20 minute period. Stirring was continued at approximately 0° C. for 1 hour and the mixture was then allowed to warm to room temperature. The reaction was allowed to stir overnight at room temperature and was heated at reflux for 3 hours. After cooling, the mixture was added to ice water and extracted with ethyl acetate. The organic layer was washed with a saturated sodium chloride solution, dried over magnesium sulfate, and concentrated in vacuo. The residue was purified by HPLC eluting with 0–10% ethylacetate in hexane, gradient. The appropriate fractions were combined and concentrated to provide 8.6 g of the desired title intermediate. NMR

PREPARATION 7

Ethyl α-hexyl-4-nitrophenylacetate

Two hundred milliliters of concentrated nitric acid were cooled to 5° C. and 200 ml of concentrated sulfuric acid were slowly added. When the temperature had returned to 5° C., 20 g of the ester from Preparation 6 above were added dropwise so as to keep the temperature at 5°-6° C. The mixture was then added to one liter of ice water, and extracted with ethyl acetate. The organic layers were combined, washed with water and a saturated sodium chloride solution, dried over magnesium sulfate and concentrated in vacuo. The residue was chromatographed by HPLC eluting first with four liters of hexane followed by a 0–10% ethyl acetate in hexane gradient. Appropriate fractions were combined and concentrated in vacuo to provide 2.7 g of the desired titled intermediate and 17 g of a mixture of other products.

Analysis for $C_{16}H_{23}NO_4$: Calc.: C, 65.51; H, 7.90; N, 4.77; Found: C, 65.64; H, 7.88; N, 4.85.

PREPARATION 8

4-Amino-α-hexyl-1H-imidazole-1-acetic acid ethyl ester

A mixture of 5.9 g of 4-nitro-a-hexyl-1H-imidazole-1-acetic acid ethyl ester, 3 g of palladium-on-carbon and 150 ml of absolute alcohol were subjected to catalytic hydrogenation. Both theoretical and actual hydrogen uptake was 73 pounds. The catalyst was removed by filtration and the filtrate concentrated in vacuo to provide 5.3 g of the desired title intermediate which was used directly.

Prepared in like manner was ethyl α-hexyl-4-aminophenylacetate from the corresponding nitro compound.

EXAMPLE 1

α-Hexyl-4-[(1-oxo-2,2-diphenylbutyl)amino]-1H-imidazole-1-acetic acid ethyl ester Five grams of 2,2-diphenylbutanoic acid were converted to the corresponding acid chloride by with 30 ml of thionyl chloride at reflux for two hours. The mixture was concentrated in vacuo and the resulting acid chloride was used directly in the next step.

To a solution of 100 ml of 20% potassium carbonate solution in 100 ml of tetrahydrofuran were added, 5.3 g of 4-amino-α-hexyl-1H-imidazole-1-acetic acid ethyl ester with stirring. The acid chloride prepared above was added as a solution in tetrahydrofuran and the mixture heated at reflux overnight. The reaction mixture was added to ice water and extracted with ethyl acetate. The organic layer was separated, washed with water, dried over sodium sulfate, and concentrated in vacuo to provide 6.0 g of the desired titled intermediate.

Analysis for $C_{29}H_{37}N_3O_3$: Calc.: C, 73.23; H, 7.84; N, 8.83; Found: C, 68.63; H, 7.17; N, 7.28.

EXAMPLE 2

4-[(3-Hydroxy-2-carboxybenzoyl)amino]-p-hexyl-1H-imidazole-1-propanoic acid methyl ester To a solution of 2.0 g of 3-hydroxyphthalic anhydride in 250 ml of absolute alcohol were added 3.0 g of 4-amino-p-hexyl-1H-imidazole-3-propanoic acid methyl ester. The mixture was stirred overnight at room temperature. The resulting white precipitate was recovered by filtration, washed with ethanol, and dried to provide 2.8 g of the desired titled intermediate.

Analysis for $C_{21}H_{27}N_3O_6$: Calc.: C, 60.42; H? 6.52; N, 10.07; Found: C, 60.33; H, 6.62; N, 9.88.

EXAMPLE 3-12

The following intermediates were prepared according to the procedure of Example 2 from the appropriate anhydride in the corresponding amine derivative. In some cases, DMF or a mixture of DMF and ethanol was used as the solvent.

3. 4-[(4-Methyl-2-carboxybenzoyl)amino]-α-hexyl-1H-imidazole-1-acetic acid methyl ester, 46% yield.

4. 4-[(3-Hydroxy-2-carboxybenzoyl)amino]-α-hexyl-1H-imidazole-1-acetic acid ethyl ester, 68% yield, m.p. 185° C.

Analysis for $C_{21}H_{27}N_3O_6$: Calc.: C, 60.42; H, 6.52; N, 10.07; Found: C, 60.60; H, 6.43; N, 10.12.

5. 4-[(2-Carboxybenzoyl)amino)-α-hexyl-1H-imidazole-1-acetic acid ethyl ester, 46% yield, m.p. 142°-143° C.

Analysis for $C_{21}H_{27}N_3O_5$: Calc.: C, 62.83; H, 6.78; N, 10.47; Found: C, 63.11; H, 6.85; N, 10.43.

6. α-Hexyl-4-{[(2-carboxyphenyl)acetyl]-amino}-1H-imidazole-1-acetic acid ethyl ester, 8.6% yield.

7. α-Hexyl-4-[[(2-carboxy-1-naphthalenyl)-carbonyl]amino}-1H-imidazole-1-acetic acid ethyl ester, 34% yield, m.p. =116°-118° C. NMR 8. 4-[(2-Carboxy-6-fluorobenzoyl)amino]-α-hexyl-1H-imidazole-1-acetic acid ethyl ester, 27% yield.

Analysis for $C_{21}H_{26}N_3O_5$ Calc.: C, 60.13; H, 6.24; N, 10.01; Found: C, 60.67; H, 6.40; N, 9.90;

9. 4-[(2-Carboxybenzoyl)amino]-α-hexylbenzeneacetic acid ethyl ester, 15% yield, m.p. =155°-156° C.

Analysis for $C_{24}H_{29}NO_5$: Calc.: C, 70.05; H, 7.10; N, 3.40; Found: C, 69.77; H, 6.99; N, 3.29.

10. 4-[(2-Carboxybenzoyl)amino]-β-hexyl-1H-imidazole-1-propanoic acid methyl ester, 42.3% yield, m.p. =125°-127° C.

Analysis for $C_{21}H_{27}N_3O_5$: Calc.: C, 62.83; H, 6.78; N, 10.47; Found: C, 62.85; H, 6.78; N, 10.30.

11. α-Hexyl-4-[(2-carboxy-6-nitrobenzoyl)-amino]-1H-imidazole-1-acetic acid ethyl ester, 95% yield. NMR.

12. 4-[(2-Carboxybenzoyl)amino]-α-hexyl-1H-imidazole-1-acetonitrile, 72.1% yield, m.p. 170°-171° C.

Analysis for $C_{19}H_{22}N_4O_3$:
Calc.: C, 64.39; H, 6.26; N, 15.81;
Found: C, 64.31; H, 6.07; N, 15.82.

EXAMPLE 13

4-[(2-Carboxybenzoyl)amino]-γ-hexyl-1H-imidazole-1-butanoic acid methyl ester

Five hundred milligrams of 4-nitro-γ-hexyl-1H-imidazole-4-non-2-enoic acid methyl ester were hydrogenated in the presence of 500 mg of 5% of palladium-on-carbon and 200 ml of absolute ethanol according to the procedure of Preparation 8. Hydrogenation reduced the nitro group to an amino group and also hydrogenated the double bond. The catalyst was removed by filtration and the resulting solution was treated with 150 mg of phthalic anhydride. After stirring at room temperature for 24 hours, the solvent was removed in vacuo and the resulting solid partitioned between ethyl acetate and water. The organic layer was separated, dried over sodium sulfate, and concentrated in vacuo. Trituration with a 1:1 mixture of hexane/ethyl acetate provided 270 mg of the desired titled intermediate, m.p. 135°-136° C.

Analysis for $C_{22}H_{29}N_3O_5$: Calc.: C, 63.60; H, 7.04; N, 10.11; Found: C, 63.66; H, 6.92; N, 9.96.

EXAMPLE 14

α-Hexyl-4-[(diphenylhydroxyacetyl)amino]-1H-imidazole-1-acetic acid ethyl ester

A mixture of 4.6 g of benzilic acid, 3.2 g of 1,1'-carbonyldiimidazole, and 150 ml of DMF were mixed and stirred for 1 hour. A solution of 5.0 g of 4-amino-α-hexyl-1H-imidazole-1-acetic acid ethyl ester in DMF was added and the mixture stirred at room temperature overnight. The reaction mixture was concentrated in vacuo, ethyl acetate was added, and the organic solution was washed sequentially with water, a 10% sodium hydroxide solution, and water. The organic layer was dried over sodium sulfate and concentrated in vacuo. The residue was purified by HPLC eluting with 30% ethyl acetate in toluene. The appropriate fractions were combined and concentrated in vacuo to provide 1.4 g of the desired titled product.

Analysis for $C_{27}H_{33}N_3O_4$: Calc.: C, 69.96; H, 7.17; N, 9.06; Found: C, 70.22; H, 7.01; N, 8.82.

EXAMPLES 15-20

The following compounds were prepared according to the procedure of Example 14 employing the appropriate carboxylic acid and the corresponding amine.

15. 4-[(9H-Fluoren-9-ylcarbonyl)amino]-α-hexyl-1H-imidazole-1-acetic acid ethyl ester, 22% yield, m.p. 150°-152° C.

Analysis for $C_{26}H_{31}N_3O_3$: Calc.: C, 72.78; H, 7.01; N, 9.43; Found: C, 72.85; H, 6.95; N, 9.22.

16. α-Hexyl-4-[(9H-xanthen-9-ylcarbonyl)-amino]-1H-imidazole-1-acetic acid ethyl ester, 9.5% yield, m.p. =177°-178° C.

Analysis for $C_{27}H_{31}N_3O_4$: Calc.: C, 70.28; H, 6.72; N, 9.11; Found: C, 70.21; H, 6.90; N, 9.12.

17. α-Hexyl-4-[(2-hydroxy-5-carboxybenzoyl)-amino]-1H-imidazole-1-acetic acid ethyl ester, 24% yield, oil.

Analysis for $C_{23}H_{31}N_3O_6$: Calc.: C, 62.00; H, 7.01; N, 9.43; Found: C, 60.28; H, 7.15; N, 10.10.

18. 4-[(9H-Fluoren-9-ylcarbonyl)amino]-α-hexylbenzeneacetic acid ethyl ester, 42% yield, m.p. 174°-175° C.

Analysis for $C_{30}H_{33}NO_3$: Calc.: C, 79.09; H, 7.30; N, 3.07; Found: C, 79.29; H, 7.24; N, 3.04.

19. α-Hexyl-3-{[(diphenylmethyl)amino]-carbonyl}phenylacetonitrile, 60% yield, m.p. 125°-128° C.

Analysis for $C_{28}H_{30}N_2O$: Calc.: C, 81.91; H, 7.36; N, 6.82; Found: C, 81.22; H, 7.16; N, 6.21.

20. α-Hexyl-4-{[2-(5-tetrazolyl)benzoyl]amino}-1H-imidazole-1-acetic acid ethyl ester, 18% yield.

Analysis for $C_{21}H_{27}N_7O_3$: Calc.: C, 58.54; H, 5.85; N, 23.90; Found: C, 58.39; H, 6.31; N, 23.44.

EXAMPLES 21-22

The following esters were prepared according to the procedure of Example 14 from the appropriate carboxylic acid and the corresponding amine employing N,N'-dicyclohexylcarbodiimide and hydroxybenzotriazole hydrate in place of the carbonyldiimidazole.

21. 4-{[2-(Ethoxycarbonylmethyl)benzoyl]-amino}-α-hexyl-1H-imidazole-1-acetic acid ethyl ester, 40% yield, oil Analysis for $C_{24}H_{33}N_3O_5$: Calc.: C, 64.99; H, 7.49; N, 9.47; Found: C, 65.25; H, 7.83; N, 9.28.

22. α-Hexyl-4-[(2-ethoxycarbonyl-3-nitro-benzoyl)amino]-1H-imidazole-1-acetic acid ethyl ester, 70% yield, m.p. 125°-127° C., MS: M+ =474.

Analysis for $C_{23}H_{30}H_4O_7$: Calc.: C, 58.23; H, 6.37; N, 11.81; Found: C, 58.64; H, 6.15; N, 11.76.

PREPARATION 9

N-(Diphenylmethyl)-1H-imidazole-4-carboxamide

A mixture of 11.7 g of 4-imidazolecarboxylic acid, 18.7 g of 1,1'-carbonyldiimidazole, 20 ml of diisopropylethylamine and 600 ml of DMF was heated at 35° C. for approximately 18 hours. Twenty milliters of aminodiphenylmethane were added and the solution stirred at 35° C. for approximately 2½ days. The mixture was concentrated in vacuo and the residue added to 400 ml of water. The mixture was extracted with ethyl acetate and the organic layer was washed with a saturated sodium chloride solution, dried over magnesium sulfate, and concentrated in vacuo. Two crystallizations from hot ethyl acetate/hexane provided 11 grams of the desired titled intermediate, m.p. 201°-202° C.

Analysis for $C_{17}H_5N_3O$: Calc.: C, 73.63; H, 5.45; N, 15.15; Found: C, 73.90; H, 5.58; N, 15.12.

EXAMPLE 23

α-Hexyl-4-{[(9H-fluoren-9-yl)amino]carbonyl}-1H-imidazole-1-acetic acid ethyl ester A slurry of 0.062 g of 55% sodium hydride in oil in tetrahydrofuran was added to 0.4 g of 4-carboxy-α-hexyl-1H-imidazole-1-acetic acid ethyl ester. After 10 minutes of stirring, 0.125 ml of oxalyl chloride were added. After stirring for 2 hours at room temperature, 0.31 g of 1-aminofluorene were added followed by 0.16 ml of pyridine. The mixture was stirred at room temperature for 3 hours, taken up in ethyl acetate,, and washed twice with a saturated citric acid solution followed by a water wash. The organic layer was dried over sodium sulfate, filtered, and concentrated in vacuo. Flash chromatography using 1:1 ethyl acetate/hexane and silica gel was performed on the residue and the resulting fractions combined and concentrated in vacuo to provide the desired titled intermediate.

EXAMPLE 24

α-Hexyl-4-{[(diphenylmethyl)amino]carbonyl}-1H-imidazole-1-acetonitrile

To a solution of 1.67 g of 4-{[(diphenyl-methyl)amino]carbonyl}-1H-imidazole in 100 ml of dimethylformamide were added 5.03 g of potassium fluoride on alumina. With stirring, 1.35 g of α-bromooctanonitrile were added. The solution was stirred at room temperature overnight and then concentrated in vacuo. The residue was taken up in ethyl acetate, washed with water, washed with a saturated sodium chloride solution, dried over magnesium sulfate, and concentrated in vacuo. NMR indicated a mixture of starting material with desired product, so the residue was dissolved in 200 ml of acetonitrile, and 1 g of α-bromooctanonitrile and 5 g of potassium fluoride on alumina was added. After stirring at room temperature for 2 days, the mixture was filtered, and the filtrate was concentrated in vacuo. The residue was chromatographed over $SiO_2$ and the appropriate fractions combined and concentrated in vacuo to provide 1.2 g of the desired titled intermediate, oil. MS: M+ =400

Analysis for $C_{25}H_{28}N_4O$: Calc.: C, 74.97; H, 7.05; N, 13.99; Found: C, 74.28; H, 6.82; N, 13.29.

EXAMPLE 25

5-Phthalimido-α-hexyl-2H-tetrazole-2-acetic acid ethyl ester

A. Preparation of 5-[(2-ethoxycarbonyl-benzoyl)amino]tetrazole.

To 50 g of oxalyl chloride were added 16.1 g of phthalic acid monomethylester. After stirring at room temperature for 2 hours, the mixture was concentrated in vacuo. The residue was added dropwise to a mixture of 9.2 g of 5-aminotetrazole, 12 ml of triethylamine, and 150 ml of DMF. After stirring for 2 hours at room temperature the mixture was filtered and the filtrate concentrated in vacuo. The resulting white solid was partitioned between water and ethyl acetate. The aqueous phase was made acidic to pH 2 and the two layers stirred overnight. The remaining white solid was recovered by filtration and dried to provide 12 g of the desired subtitled intermediate, m.p. 257° C. (decomposition).

Analysis for $C_{10}H_9N_5O_3$: Calc.: C, 48.59; H, 3.67; N, 28.33; Found: C, 48.37; H, 3.71; N, 28.55.

B. Preparation of 5-phthalimido-α-hexyl-2H-tetrazole-2-acetic acid ethyl ester.

A mixture of 5 g of the tetrazole amide from Example 25A above, 5.6 g of ethyl 2-bromooctanoate, 3.4 g of sodium bicarbonate, and 200 ml of DMF was heated at 75° C. for 2.5 hours. The solution was allowed to cool to room temperature and then concentrated in vacuo. The residue was partitioned between water and ethyl acetate and the aqueous layer adjusted to pH 2.5 with 1N hydrochloric acid. The solution was extracted twice with ethyl acetate. The organic layers were combined, washed with water and a saturated sodium chloride solution, dried over magnesium sulfate, and concentrated in vacuo. The resulting solid was triturated with diethyl ether. The ether was separated filtered, and concentrated to provide 6.5 g of an oil which contained both the N-1 and N-2 isomers. This material was purified by HPLC using a 0-60% ethyl acetate in hexane gradient to provide 3.4 g of the desired N-2 isomer and 0.6 g of the undesired N-1 isomer, oil. NMR.

EXAMPLE 26

α-Hexyl-4-[(1-oxo-2,2-diphenylbutyl)amino]-1H-imidazole-1-acetic acid

A mixture of 6 g of α-hexyl-4-[(1-oxo-2,2-diphenylbutyl)amino]-1H-imidazole-1-acetic acid ethyl ester, 50 ml of 1N sodium hydroxide, and 100 ml of methanol were stirred at room temperature for 1 hour. The mixture was concentrated in vacuo, taken up in water, and the pH adjusted to 4.0. The aqueous solution was extracted with ethyl acetate. The organic extract was washed twice with water, dried over sodium sulfate, and concentrated in vacuo. The residue was dissolved in methylene chloride filtered, and concentrated in vacuo to provide 2.4 g of the desired titled product.

Analysis for $C_{27}H_{33}N_3O_3$: Calc.: C, 72.46; H, 7.43; N, 9.39; Found: C, 72.20; H, 7.50; N, 9.39.

EXAMPLES 27–45

The following acids were prepared according to the procedure of Example 26 employing the appropriate ester intermediate; in some cases, potassium hydroxide was used in place of sodium hydroxide. The hydrochloride salts were formed by dissolving the acid in ethyl acetate, adding 10% hydrochloric acid, and removing the salt by filtration.

27. β-Hexyl-4-[(2-carboxy-3-hydroxybenzoyl)-amino]-1H-imidazole-1-propanoic acid hydrate, 86% yield.

Analysis for $C_{20}H_{25}N_3O_6.H_2O$: Calc.: C, 58.00; H, 6.46; N, 9.97; Found: C, 58.01; H, 6.03; N, 9.89.

28. α-Hexyl-4-[(2-carboxy-4-methylbenzoyl)-amino]-1H-imidazole-1-acetic acid, 27% yield.

Analysis for $C_{20}H_{25}N_3O_5$: Calc.: C, 62.00; H, 6.50; N, 10.85; Found: C, 61.77; H, 6.39; N, 10.69.

29. α-Hexyl-[(hydroxydiphenylacetyl)amino]-1H-imidazole-1-acetic acid hydrochloride, 57% yield.

Analysis for $C_{25}H_{29}N_3O_4.HCl$: Calc.: C, 63.62; H, 6.41; N, 8.90; Found: C, 63.41; H, 6.27; N, 8.80.

30. α-Hexyl-4-[(2-carboxy-3-hydroxybenzoyl)-amino]-1H-imidazole-1-acetic monohydrate, 20% yield.

Analysis for $C_{19}H_{23}N_3O_6.H_2O$: Calc.: C, 55.96; H, 6.10; N, 10.32; Found: C, 55.84; H, 5.66; N, 10.29.

31. α-Hexyl-9-[(9H-fluoren-9-ylcarbonyl)-amino]-1H-imidazole-1-acetic acid hydrochloride, 60% yield.

Analysis for $C_{25}H_{27}N_3O_3.HCl$: Calc.: C, 66.23; H, 6.18; N, 9.27; Found: C, 66.34; H, 6.19; N, 9.27.

32. α-Hexyl-4-[(9H-xanthen-9-ylcarbonyl)-amino]-1H-imidazole-1-acetic acid hydrochloride monohydrate, 55% yield, m.p. 185°–188° C.

Analysis for $C_{25}H_{27}N_3O_4.HCl.H_2O$: Calc.: C, 61.53; H, 6.20; N, 8.61; O, 16.36; Cl, 7.27; Found: C, 61.45; H, 6.33; N, 7.87; O, 15.90; Cl, 6.53.

33. 4-[(2-Carboxybenzoyl)amino]-α-hexyl-1H-imidazole-1-acetic acid, 35% yield.

Analysis for $C_{19}H_{23}N_3O_5$: Calc.: C, 61.12; H, 6.21; N, 11.25; Found: C, 61.12; H, 5.93; N, 11.01.

34. α-Hexyl-4-{[(2-carboxyphenyl)acetyl]-amino}-1H-imidazole-1-acetic acid hydrate, 3.5% yield.

Analysis for $C_{20}H_{25}N_3O_5.H_2O$: Calc.: C, 59.11; H, 6.65; N, 10.34; Found: C, 59.41; H, 6.35; N, 10.14.

35. α-Hexyl-4-{[(2-carboxy-1-naphthalenyl)-carbonyl]amino}-1H-imidazole-1-acetic acid, 24% yield.

Analysis for $C_{23}H_{25}N_3O_5$: Calc.: C, 64.24; H, 5.95; N, 9.92; Found: C, 64.96; H, 6.07; N, 10.16.

36. α-Hexyl-4-[(2-hydroxy-5-carboxybenzoyl)-amino]-1H-imidazole-1-acetic acid, 64% yield.

Analysis for $C_{19}H_{23}N_3O_6$: Calc.: C, 58.60; H, 5.95; N, 10.79; Found: C, 58.39; H, 5.76; N, 10.55.

37. 4-[(2-Carboxy-6-fluorobenzoyl)amino]-α-hexyl-1H-imidazole-1-acetic acid hydrate (1:2.5), 76% yield.

Analysis for $C_{19}H_{22}N_3FO_5.2.5\ H_2O$: Calc.: C, 52.28; H, 6.23; N, 9.62; Found: C, 52.52; H, 6.16; N, 9.16.

38. α-Hexyl-4-[(2-carboxybenzoyl)amino]-benzeneacetic acid, 35% yield, m.p. 159°–161° C.

Analysis for $C_{22}H_{25}NO_5$: Calc.: C, 68.91; H, 6.57; N, 3.65; Found: C, 68.62; H, 6.48; N, 3.53.

39. 4-[(2-Carboxybenzoyl)amino]-β-hexyl-H-imidazole-1-propanoic acid monohydrate, 82.5% yield, m.p. 98°–100° C.

Analysis for $C_{20}H_{25}N_3O_5.H_2O$: Calc.: C, 59.24; H, 6.71; N, 10.36; Found: C, 59.49; H, 6.36; N, 10.26.

40. α-Hexyl-4-[(2-carboxy-6-nitrobenzoyl)-amino]-1H-imidazole-1-acetic acid, 16% yield, m.p. 161°–163° C.

Analysis for $C_{19}H_{22}N_4O_7$: Calc.: C, 54.54; H, 5.30; N, 13.39; Found: C, 54.39; H, 5.24; N, 13.12.

41. 4-[(2-Carboxybenzoyl)amino]-γ-hexyl-1H-imidazole-1-butanoic acid hemihydrate, 75% yield, m.p. 83°–85° C.

Analysis for $C_{21}H_{27}N_3O_5.0.5\ H_2O$: Calc.: C, 61.45; H, 6.88; N, 10.24; Found: C, 61.60; H, 6.60; N, 10.25.

42. α-Hexyl-4-{[2-(tetrazol-5-yl)benzoyl]-amino}-1H-imidazole-1-acetic acid monohydrate, 10% yield. NMR, MS.

Analysis for $C_{19}H_{23}N_7O_3.H_2O$: Calc.: C, 55.10; H, 5.36; N, 25.00; Found: C, 55.42; H, 5.80; N, 22.72.

43. 4-{[2-(Carboxymethyl)benzoyl]amino}-α-hexyl-1H-imidazole-1-acetic acid monohydrate, 14% yield.

Analysis for $C_{20}H_{25}N_3O_5.H_2O$: Calc.: C, 59.16; H, 6.64; N, 10.34; Found: C, 58.81; H, 6.21; N, 10.49.

44. α-Hexyl-4-{[(9H-fluoren-9-yl)amino]-carbonyl}-1H-imidazole-1-acetic acid hydrochloride, 73% yield.

Analysis for $C_{25}H_{27}N_3O_3.HCl$: Calc.: C, 66.14; H, 6.22; N, 9.26; Found: C, 67.80; H, 6.76; N, 9.37.

45. α-Hexyl-4-[(2-carboxy-3-nitrobenzoyl)-amino]-1H-imidazole-1-acetic acid hydrate, 30% yield, m.p. 151°–153° C.

Analysis for $C_{19}H_{22}N_4O_7.H_2O$: Calc.: C, 52.29; H, 5.54; N, 12.84; Found: C, 52.30; H, 5.06; N, 12.50.

EXAMPLE 46

α-Hexyl-4-[(9-hydroxy-9H-fluoren-9-ylcarbonyl)-amino]benzeneacetic acid

The titled product was prepared in 76% yield from α-hexyl-4-[(9H-fluoren-9-ylcarbonyl)amino]benzene acetic acid ethyl ester according to the procedure of Example 26, m.p. 183°–185° C.

Analysis for $C_{28}H_{29}NO_4$: Calc.: C, 75.82; H 6.59; N, 3.16; Found: C, 75.71; H, 6.62; N, 3.07.

EXAMPLE 47

5-[(2-Carboxybenzoyl)amino]-α-hexyl-2H-tetrazole-2-acetic acid

The titled product was prepared in 41% yield from a-hexyl-5-phthalimido-2H-tetrazole-2-acetic acid ethyl ester according to the procedure of Example 26, m.p. 140°–142° C.

Analysis for $C_{17}H_{21}N_5O_5$: Calc.: C, 54.39; H, 5.64; N, 18.66; Found: C, 54.49; H, 5.69; N, 18.43.

EXAMPLE 48

1-[1-(Tetrazol-5-yl)heptyl]-N-(diphenylmethyl)-1H-imidazole-4-carboxamide

To a solution of 1.22 g of 4-{[(diphenylmethyl)amino]carbonyl}-α-1H-imidazole-1-acetonitrile in 175 ml of dimethoxyethylene were added 1.11 g of sodium azide and 2.22 g of triethylamine hydrochloride. The mixture was heated at reflux for 21 hours under a nitrogen atmosphere. The reaction was allowed to cool, the solid was removed by filtration, and the filtrate was concentrated in vacuo. The resulting oil was dissolved in methanol and methanolic hydrogen chloride was added. After 30 minutes, the solvent was evaporated. The residue was taken up in hot ethyl acetate and filtered. The filtrate was evaporated and the residue dissolved in diethyl ether, layered with water, and the pH adjusted to 8.0 with 1N sodium hydroxide. The organic layer was washed with a saturated sodium chloride solution, dried over magnesium sulfate, and concentrated in vacuo to provide 0.3 g (11%) of the titled product as a glass-like solid. MS: M+ =444.

Analysis for $C_{25}H_{29}N_7O$: Calc.: C, 67.70; H, 6.59; N, 22.11; Found: C, 67.71; H, 6.34; N, 21.93.

EXAMPLE 49

N-(Diphenylmethyl)-3-[1-(tetrazol-5-yl)-heptyl]benzamide

The titled product was prepared in 35% yield from the corresponding nitrile intermediate according to the procedure of Example 48, m.p. 198°–200° C.

Analysis for $C_{28}H_{31}N_5O$: Calc.: C, 74.14; H, 6.89; N, 15.44; Found: C, 73.94; H, 6.70; N, 15.20.

EXAMPLE 50

2-[({1-[1-(Tetrazol-5-yl)heptyl]-1H-imidazol-4-yl}amino)carbonyl]benzoic acid hemihydrate To 700 mg of α-hexyl-4-[(2-carboxybenzoyl)-amino]-1H-imidazole-1-acetonitrile were added 2.0 g of tributyl tin azide. The mixture was heated at 85° C. for 2 days, cooled, and added to 50 ml of methanol previously saturated with hydrogen chloride gas. After stirring for 20 minutes, the solvent was removed in vacuo. The residue was triturated with diethyl ether. The remaining solid was diluted with 100 ml of absolute ethanol and 100 ml of 4N sodium hydroxide. After stirring for two hours, the solution was concentrated in vacuo. The residue was taken up in water and the pH adjusted to 3.7. The aqueous solution was extracted with ethyl acetate. The organic layer was dried over sodium sulfate and concentrated in vacuo. The resulting solid was slurried with diethyl ether and filtered to provide 150 mg of the desired titled product, m.p. 120°–121° C.

Analysis for $C_{19}H_{23}N_7O_3.0.5\ H_2O$: Calc.: C, 56.15; H, 5.95, N, 24.10; Found: C, 56.12; H, 5.84, N, 23.97.

EXAMPLE 51

α-Hexyl-4-[(diphenylacetyl)amino]-1H-imidazole-1-acetic acid hydrochloride

Following the procedure of Example 14, 637 mg of diphenylacetic acid and 486 mg of carbonyldiimidazole were allowed to react in 10 ml of DMF. After stirring at room temperature for 60 minutes, 750 mg of 4-amino-α-hexyl-1H-imidazole-1-acetic acid ethyl ester were added as a solution in 10 ml of DMF. The reaction was stirred overnight at room temperature, concentrated in vacuo, and worked up in the usual manner. The resulting ester was then hydrolyzed according to the procedure of Example 26 to provide 250 mg of the desired titled product.

Analysis for $C_{25}H_{29}N_3O_3.HCl$: Calc.: C, 65.85; H, 6.63; N, 9.22; Found: C, 69.35; H, 7.80; N, 10.32.

EXAMPLE 52

α-Hexyl-3-{([(diphenylmethyl)amino]carbonyl}-1H-1,2,4-triazole-1-acetic acid hydrochloride Following the general procedure of Example 25B, 1.2 g of 3-{[(diphenylmethyl)amino]carbonyl}-1H-1,2,4-triazole in 30 ml of DMF were treated with 0.93 ml of ethyl 2-bromooctanoate and 188 mg of 55% sodium hydride. After stirring at room temperature overnight, the reaction was worked up in the usual manner. The resulting ester was hydrolyzed according to the procedure of Example 26 to provide 300 mg of the desired titled product.

Analysis for $C_{24}H_{28}N_4O_3.HCl$: Calc.: C, 68.55; H, 6.71; N, 13.3; Found: C, 66.91; H, 6.71; N, 12.75.

EXAMPLES 53 AND 54

The following compounds were prepared in the same manner as described in Example 52 beginning with the appropriate heterocyclic amide.

53. 3-{[(Diphenylmethyl)amino]carbonyl}-α-hexyl-1H-pyrrole-1-acetic acid, 48% yield.

Analysis for $C_{26}H_{30}N_2O_3$: Calc.: C, 73.86; H, 7.44; N, 6.89; Found: C, 74.37; H, 7.08; N, 6.45.

54. 4-{[(Diphenylmethyl)amino]carbonyl}-α-hexyl-1H-pyrazole-1-acetic acid, 68% yield.

Analysis for $C_{25}H_{29}N_3O_3$: Calc.: C, 71.75; H, 6.97; N, 11.40; Found: C, 71.23; H, 7.10; N, 10.04.

EXAMPLE 55

α-Pentyl-4-(2-carboxyphenoxy)phenylacetic acid

A. Preparation of 4-(2-ethoxycarbonylphenoxy)-phenylheptanone.

To a mixture of 55 g of ethyl 2-phenoxybenzoate and 35 ml of heptanoyl chloride were added 35 g of aluminum trichloride. After heating at reflux for 16 hours, an additional 60 g of aluminum chloride were added and the reaction heated at reflux an additional 16 hours. The reaction mixture was poured over ice and concentrated hydrochloric acid. The organic layer was separated, dried, and concentrated in vacuo The residue was purified by HPLC eluting with 5–25% ethyl acetate in hexane. The appropriate fractions were combined and concentrated in vacuo to provide 11.2 g of the desired subtitled intermediate, m.p. 54°–55° C.

Analysis for $C_{22}H_{26}O_4$: Calc.: C, 74.55; H, 7.39; Found: C, 74.84; H, 7.46.

B. Preparation of α-pentyl-4-(2-ethoxycarbonylphenoxy)phenylacetic acid methyl ester.

To 5.3 g of the ketone intermediate from Example 55A above in 8 ml of trimethylorthoformate were added 7.62 g of iodine. The reaction mixture was stirred at room temperature for 24 hours at which time an additional 2 ml of trimethoxyorthoformate were added. After stirring an additional 24 hours, aqueous 10% sodium thiosulfate was added. After stirring for one hour, the product was extracted into ethyl acetate. The organic layer was dried, concentrated in vacuo to provide 5.2 g of the desired subtitled intermediate.

Analysis for $C_{23}H_{28}O_5$: Calc.: C, 71.85; H, 7.34; Found: C, 71.65; H, 7.40.

C. Preparation of α-pentyl-4-(2-carboxyphenoxy)-phenylacetic acid.

Following the procedure of Example 26, 4 g of the ester intermediate from Example 55B above were heated with ethanol and sodium hydroxide solution to provide 2.7 g of the desired titled product, m.p. 112°–113° C.

Analysis for $C_{20}H_{22}O_5$: Calc.: C, 70.16; H, 6.48; Found: C, 70.25; H, 6.58.

EXAMPLE 56

α-Hexyl-4-(2-carboxybenzoyl)benzeneacetic acid

The ethyl ester of the titled product was prepared in 18% yield by reacting phthalic anhydride and α-hexyl-benzeneacetic acid ethyl ester in the presence of aluminum chloride in DMF according to the general procedure of Example 55. The title product was then prepared according to the procedure of Example 26 in 45% yield from the intermediate ester, m.p. 118°–121° C.

Analysis for $C_{22}H_{24}O_5$: Calc.: C, 71.72; H, 6.56; Found: C, 71.57; H, 6.32.

EXAMPLES 57–58

The following products were prepared according to the procedure of Example 14 by first reacting ethyl 4-carboxy-α-hexyl-1H-imidazole-1-acetate and carbonyldiimidazole in dimethylformamide together with the appropriate amine to provide the corresponding ester intermediate which was then hydrolyzed according to the procedure of Example 26 to provide the final products as indicated.

57. 4-{[(2,3-Dihydro-1H-inden-1-yl)aminol-carbonyl}-α-hexyl-1H-imidazole-1-acetic acid hydrochloride, 83% yield.

Analysis for $C_{21}H_{27}N_3O_3 \cdot HCl$: Calc.: C, 62.14; H, 6.95; N, 10.35; Found: C, 62.35; H, 7.17; N, 10.18.

58. 4-{[(Diphenylmethyl)amino]carbonyl}-α-hexyl-1H-imidazole-1-acetic acid hydrochloride, 64% yield.

Analysis for $C_{25}H_{29}N_3O_3 \cdot HCl$: Calc.: C, 65.85; H, 6.63; N, 9.22; Found: C, 65.97; H, 6.51; N, 9.43.

EXAMPLE 59

α-Hexyl-4-[(9-hydroxy-9H-fluoren-9-ylcarbonyl)-amino]-1H-imidazole-1-acetic acid When 2.1 g of α-hexyl-4-[(9H-fluoren-9-yl-carbonyl)amino]-1H-imidazole-1-acetic acid ethyl ester was heated with 3.0 g of potassium hydroxide, 30 ml of methanol, and 15 ml of water at reflux for one hour, upon adjustment of pH to 3.8, a thick oil formed. The oil was dissolved in ethyl acetate and separated from the aqueous layer. The organic layer was dried and concentrated in vacuo. The oil was taken up in ethanol and saturated with hydrogen chloride gas. The resulting product was purified by high pressure liquid chromatography to provide 0.3.70 g of the titled product, m.p. 128° C.

Analysis for $C_{25}H_{27}N_3O_4$: Calc.: C, 69.27; H, 6.28; N, 9.69; Found: C, 69.03; H, 6.37; N, 9.43.

EXAMPLE 60

2-[({1-[1-(Hydroxymethyl)hexyl]-1H-imidazol-4-yl}amino)carbonyl]benzoic acid

Seven hundred milligrains of 4-nitro-β-hexyl-H-imidazole-2-ethanol in 100 ml of absolute ethanol and 200 mg of 5% palladium-on-carbon were hydrogenated. The reaction mixture was filtered and added directly to a stirred solution of 473 mg of phthalic anhydride in 50 ml of absolute ethanol and 10 ml of dimethylformamide. The reaction was stirred at room temperature overnight. The solvent was removed in vacuo and diluted in 100 ml of 1N sodium hydroxide solution. After stirring for 30 minutes, the mixture was washed with diethyl ether. The aqueous layer was adjusted to pH 3.5 with 6N hydrochloric acid. The aqueous solution was extracted into ethyl acetate. The organic layer was dried over sodium sulfate, and concentrated in vacuo to provide 1.0 g of the desired title product, m.p. 99°–101° C.

Analysis for $C_{18}H_{23}N_3O_4$: Calc.: C, 62.59; H, 6.71; N, 12.16; Found: C, 62.45; H, 6.71; N, 11.89.

EXAMPLE 61–65

The following benzamide intermediates were prepared according to the procedure of Examples 21–22.

61. α-Hexyl-4-[(2-hydroxybenzoyl)amino]-1H-imidazole-1-acetic acid ethyl ester, 46% yield.

Analysis for $C_{20}H_{27}N_3O_4$: Calc.: C, 64.32; H, 7.28; N, 11.25; Found: C, 64.31; H, 7.77; N, 11.79.

62. α-Hexyl-4-{[(2-hydroxy-1-naphthalenyl)-carbonyl]amino}imidazole-1-acetic acid ethyl ester.

63. α-Hexyl-4-[(3-hydroxybenzoyl)amino]-1H-imidazole-1-acetic acid ethyl ester, 93% yield. MS.

64. α-Hexyl-4-[(3,4-dihydroxybenzoyl)amino]-1H-imidazole-1-acetic acid ethyl ester, 37% yield.

Analysis for $C_{20}H_{27}N_3O_5$: Calc.: C, 61.68; H, 6.99; N, 10.79; Found: C, 59.70; H, 6.04; N, 13.38.

65. α-Hexyl-4-[(3,5-dihydroxybenzoyl)amino]-1H-imidazole-1-acetic acid ethyl ester, 58% yield.

Analysis for $C_{20}H_{27}N_3O_5$: Calc.: C, 61.68; H, 6.99; N, 10.79; Found: C, 58.68; H, 6.64; N, 11.91.

EXAMPLES 66–75

The following imidazole carboxamide derivatives were prepared from the appropriate imidazole carboxylic acid and corresponding aniline derivative according to the procedure of Examples 14 and 47–58 above.

66. α-Hexyl-4-({[(4-hydroxyphenyl)methyl]-amino}carbonyl)-1H-imidazole-1-acetic acid ethyl ester.

67. α-Hexyl-4-{[(2-hydroxyphenyl)amino]-carbonyl}-1H-imidazole-1-acetic acid ethyl ester.

68. α-Hexyl-4-({[2-(hydroxymethyl)phenyl]-amino}carbonyl)-1H-imidazole-1-acetic acid ethyl ester.

69. α-Hexyl-4-({[2-(4-hydroxybutyl)phenyl]-amino}carbonyl)-1H-imidazole-1-acetic acid ethyl ester.

70. α-Hexyl-4-({[3-(hydroxymethyl)phenyl]-amino}carbonyl)-1H-imidazole-1-acetic acid ethyl ester.

71. α-Hexyl-4-({[2-(2-hydroxyethyl)phenyl]-amino}carbonyl)-1H-imidazole-1-acetic acid ethyl ester.

72. α-Hexyl-4-({[4-(2-hydroxyethyl)phenyl]-amino}carbonyl)-1H-imidazole-1-acetic acid ethyl ester.

73. α-Butyl-4-{[(4-hydroxyphenyl)amino]-carbonyl}-1H-imidazole-1-acetic acid ethyl ester.

74. α-Butyl-4-{[(3-hydroxyphenyl)amino]-carbonyl}-1H-imidazole-1-acetic acid ethyl ester.

75. α-Butyl-4-{[(2-hydroxyphenyl)amino]-carbonyl}-1H-imidazole-1-acetic acid ethyl ester.

EXAMPLES 76–89

The following carboxylic acids were prepared from the corresponding esters according to the general procedure of Example 26.

76. α-Hexyl-4-[(2-hydroxybenzoyl)amino]-H-imidazole-1-acetic acid, 89% yield.

Analysis for $C_{18}H_{23}N_3O_4$: Calc.: C, 62.59; H, 6.71; N, 12.17; Found: C, 62.63; H, 6.60; N, 11.89.

77. α-Hexyl-4-{[(2-hydroxy-1-naphthalenyl)-carbonyl]amino}imidazole-1-acetic acid, 2.8% yield.

Analysis for $C_{22}H_{25}N_3O_4$: Calc.: C, 66.82; H, 6.37; N, 10.63; Found: C, 66.95; H, 6.13; N, 10.41.

78. α-Hexyl-4-[(3-hydroxybenzoyl)amino]-1H-imidazole-1-acetic acid hemihydrate, 77% yield.

Analysis for $C_{18}H_{23}N_3O_4 \cdot 0.5\ H_2O$: Calc.: C, 60.93; H, 6.77; N, 11.85; Found: C, 60.59; H, 6.60; N, 11.59.

79. α-Hexyl-4-[(3,4-dihydroxybenzoyl)amino]-H-imidazole-1-acetic acid (1.75 hydrate), 50% yield.

Analysis for $C_{18}H_{23}N_3O_5 \cdot 1.75\ H_2O$: Calc.: C, 55.01; H, 6.61; N, 10.68; Found: C, 54.92; H, 6.19; N, 10.49.

80. α-Hexyl-4-[(3,5-dihydroxybenzoyl)amino]-1H-imidazole-1-acetic acid (0.75 hydrate), 62% yield.

Analysis for $C_{18}H_{23}N_3O_5 \cdot 0.75\ H_2O$: Calc.: C, 67.75; H, 6.42; N, 11.23; Found: C, 57.54; H, 6.49; N, 11.69.

81. α-Hexyl-4-({[(4-hydroxyphenyl)methyl]-amino}carbonyl)-1H-imidazole-1-acetic acid hydrochloride, yield. MS:M+ = 360.

82. α-Hexyl-4-{[(2-hydroxyphenyl)amino]-carbonyl}-1H-imidazole-1-acetic acid hydrochloride. MS:M+ = 317.

83. α-Hexyl-4-({[2-(hydroxymethyl)phenyl]-amino}carbonyl)-1H-imidazole-1-acetic acid hydrochloride, 94% yield.

Analysis for $C_{19}H_{25}N_3O_4 \cdot HCl$: Calc.: C, 57.65; H, 6.62; N, 10.61; Found: C, 57.51; H, 6.85; N, 10.43.

84. α-Hexyl-4-({[2-(4-hydroxybutyl)phenyl]-amino}carbonyl)-1H-imidazole-1-acetic acid hydrochloride, 82% yield.

Analysis for $C_{22}H_{41}N_3O_4 \cdot HCl$: Calc.: C, 60.33; H, 7.37; N, 9.59; Found: C, 60.55; H, 7.43; N, 9.46.

85. α-Hexyl-4-({[3-(hydroxymethyl)phenyl]-amino}carbonyl)-1H-imidazole-1-acetic acid hydrochloride, Analysis for $C_{19}H_{25}N_3O_4 \cdot HCl$: Calc.: C, 57.64; H, 6.62; N, 10.61; Found: C, 57.85; H, 6.74; N, 10.36.

86. α-Hexyl-4-({[2-(2-hydroxyethyl)phenyl]-amino}carbonyl)-1H-imidazole-1-acetic acid hydrochloride, 98% yield.

Analysis for $C_{20}H_{27}N_3O_4 \cdot HCl$: Calc.: C, 58.60; H, 6.89; N, 10.25; Found: C, 58.37; H, 7.04; N, 9.55.

87. α-Hexyl-4-({[4-(2-hydroxyethyl)phenyl]-amino}carbonyl)-1H-imidazole-1-acetic acid hydrochloride, Analysis for $C_{20}H_{27}N_3O_4 \cdot HCl$: Calc.: C, 58.60; H, 6.89; N, 10.25; Found: C, 58.62; H, 6.77; N, 10.53.

88. α-Butyl-4-{[(4-hydroxyphenyl)amino]-carbonyl}-1H-imidazole-1-acetic acid hydrochloride. MS:M+ = 317.

89. α-Butyl-4-{[(2-hydroxyphenyl)amino]-carbonyl}-1H-imidazole-1-acetic acid hydrochloride. MS:M+ = 317.

EXAMPLE 90

4-[(2-Ethoxycarbonylphenyl)methyl]-α-hexylbenzeneacetic acid methyl ester

A. Preparation of 2-benzylbenzoic acid ethyl ester.

To a solution of 10.05 g of α-phenyl-o-toluic acid in ethanol was bubbled hydrogen chloride gas for 20 minutes. The mixture was then heated at reflux for 6 hours and stirred overnight at room temperature. The solvent was removed by evacuation and the residue taken up in diethyl ether. The ether solution was washed with a dilute sodium hydroxide solution, water, and a saturated sodium chloride solution, dried over magnesium sulfate, and concentrated in vacuo to provide 11 g of the desired subtitled intermediate. NMR.

B. Preparation of 2-(4-octanoylbenzyl)benzoic acid ethyl ester.

To a solution of 10.8 g of the ester from Example 90A above in dichloromethane cooled to approximately 0° C. were added 15.1 g of aluminum chloride. A solution of 7.7 g of octanoyl chloride in methylene chloride was added dropwise over a 45-minute period. The mixture was allowed to warm to room temperature and stirred for 18 hours. The mixture was poured into a mixture of ice in concentrated hydrochloric acid. After stirring for one hour, the layers were separated and the organic layer washed with a saturated sodium chloride solution, dried over magnesium sulfate, and concentrated in vacuo. The resulting oil was purified by high pressure liquid chromatography eluting with a 0–30% ethyl acetate in hexane gradient. The appropriate fractions were combined and evaporated to provide 9.5 g of the desired subtitled intermediate. NMR.

Analysis for $C_{24}H_{30}O_3$: Calc.: C, 78.65; H, 8.25; Found: C, 78.76; H, 7.95.

C. Preparation of 4-[(2-ethoxycarbonyl-phenyl)methyl]-α-hexylbenzeneacetic acid methyl ester.

Following the procedure of Example 55B, 3.67 g of the ester intermediate from Example 90B above, 5.1 g of iodine, and 5.5 ml of trimethylorthoformate were allowed to react to provide 3.6 g of the desired titled intermediate. NMR, MS.

EXAMPLE 91

2'-Ethoxycarbonyl-α-hexyl-4-biphenylacetonitrile

A. Preparation of 2-phenylbenzoic acid ethyl ester.

In the same way as provided in Example 90A, 30 g of 2-phenylbenzoic acid were treated with hydrogen chloride gas in ethanol and worked up to provide 34 g of the desired subtitled intermediate. NMR.

B. Preparation of 2-(4-heptanoylphenyl)-benzoic acid ethyl ester.

Following the procedure of Example 90B, 29 g of the ester from Example 91A above, 21 ml of heptanoyl chloride, 41.5 g of aluminum chloride, and 750 ml of dichloromethane were allowed to react provided 6.5 g of the desired subtitled intermediate. NM, MS.

Analysis for $C_{22}H_{26}O_3$: Calc.: C, 78.08; H, 7.74; Found: C, 78.25; H, 7.91

C. Preparation of 4-(2-ethoxycarbonylphenyl)-α-hexylbenzyl alcohol.

To 5.2 g of the ketone intermediate from Example 91B above in 75 ml of ethanol cooled to approximately 0° C. were added 0.6 g of sodium borohydride. After stirring in the cold for 30 minutes, the reaction mixture was allowed to warm to room temperature and stirred under a nitrogen blanket for 1.5 hours. The solvent was removed in vacuo and the residue taken up in ethyl acetate. The organic layer was washed with dilute hydrochloric acid. The aqueous layer was back extracted with ethyl acetate and the combined organic phases were washed with a saturated sodium chloride solution, dried over magnesium sulfate, and concentrated in vacuo to provide 5.0 g of the desired subtitled intermediate. NM. MS.

Analysis for $C_{22}H_{28}O_3$: Calc.: C, 77.61; H, 8.29; Found: C, 77.80; H, 8.22.

D. Preparation of 4-(2-ethoxycarbonylphenyl)-α-hexylbenzyl bromide.

Four grams of the alcohol intermediate from Example 91C above were dissolved in 150 ml of methylene chloride and cooled by means of an external ice bath. Under a nitrogen atmosphere, a solution of 1.3 ml of phosphorus tribromide in methylene chloride was added dropwise over a period of 35 minutes. Stirring was continued for one hour, the ice bath was removed, and the solution was allowed to warm to room temperature for one hour. The solution was added to a mixture of ice and concentrated hydrochloric acid and, after reaching room temperature, was extracted with ethyl acetate. The organic layer was washed sequentially with water and a saturated sodium chloride solution, dried over magnesium sulfate, and concentrated in vacuo to provide 4.3 g of the desired subtitled intermediate. NMR. MS.

Analysis for $C_{22}H_{27}BrO_2$ Calc.: C, 65.51; H, 6.75; Found: C, 65.74; H, 6.64.

E. Preparation of 2'-ethoxycarbonyl-α-hexyl-4-biphenylacetonitrile.

A solution of 3.1 g of the bromo intermediate from Example 91D above and 0.42 g of sodium cyanide in 30 ml of dimethylsulfoxide was heated to 60°-75° C. for 13 hours. An additional 0.1 g of sodium cyanide was added and heating continued an additional 2 hours. The solution was added to 600 ml of water and 400 ml of ethyl acetate. After adding dry sodium chloride, the layers were separated. The organic layer was washed with water and a saturated sodium chloride solution, dried over magnesium sulfate and concentrated in vacuo. High pressure liquid chromatography eluting first with two liters of hexane followed by a 0-25% ethyl acetate in hexane gradient and combination and evaporation of the relevant fractions provided 1.4 g of the desired subtitled intermediate. NMR. MS.

EXAMPLE 92

α-Hexyl-4-{[(3-amino-2-ethoxycarbonylphenyl)-carbonyl]amino}imidazole-1-acetic acid ethyl ester A mixture of 5.1 g of a-hexyl-4-{[(3-nitro-2-ethoxycarbonylphenyl)carbonyl]amino}imidazole-1-acetic acid ethyl ester and 2.1 g of 5% palladium-on-carbon were hydrogenated in the presence of 150 ml of methanol until consumption of hydrogen ceased. The catalyst was removed by filtration and the filtrate concentrated in vacuo to provide 4.7 g of the desired subtitled intermediate. NMR.

EXAMPLE 93

α-Hexyl-4-{[3-(acetylamino)-2-carboxybenzoyl]-amino}-1H-imidazole-1-acetic acid ethyl ester Following the procedure of Example 2, 1.54 g of 4-nitro-α-hexyl-1H-imidazole-1-acetic acid ethyl ester were hydrogenated to the corresponding amine and allowed to react with 1.12 g of 3-acetamidophthalic anhydride in ethyl acetate. After stirring at room temperature, the solution was concentrated in vacuo and a small amount ethyl acetate added. After sitting overnight, the resulting solid was collected by filtration. Crystallization from hot ethyl acetate/methanol/hexanes provided 0.54 g of the desired intermediate, m.p. 144°-145° C. NMR.

Analysis for $C_{23}H_{30}N_4O_6$: Calc.: C, 50.25; H, 6.59; N, 12.22; Found: C, 50.03; H, 6.55; N, 12.26.

EXAMPLE 94-97

The following carboxylic acid derivatives were prepared from the corresponding esters according to the procedure of Example 26.

94. 4-[(2-Carboxyphenyl)methyl]-α-hexylbenzeneacetic acid, 66% yield, m.p. 119°-121° C. NM, MS.

Analysis for $C_{22}H_{26}O_4$: Calc.: C, 74.55; H, 7.39; Found: C, 74.39; H, 7.53.

95. α-Hexyl-2'-carboxy-4-biphenylacetic acid.

96. α-Hexyl-4-[(3-amino-2-carboxybenzoyl)-amino]-1H-imidazole-1-acetic acid, 95% yield.

Analysis for $C_{19}H_{24}N_4O_5$: Calc.: C, 58.75; H, 6.23; N, 14.42; Found: C, 58.54; H, 5.95; N, 14.16.

97. α-Hexyl-4-{[3-(acetylamino)-2-carboxy-benzoyl]amino}-1H-imidazole-1-acetic acid hemihydrate, m.p. 100°-104° C., 16% yield.

Analysis for $C_{21}H_{26}N_4O_6 \cdot 0.5\ H_2O$: Calc.: C, 57.40; H, 6.19; N, 12.75; Found: C, 57.24; H, 5.93; N, 12.57.

The compounds of Formula I are potent effective antagonists of angiotensin II. As such, they are useful for treating angiotensin-induced hypertension in mammals and will also be useful for the treatment of congestive heart failure. The ability for compounds of Formula I to block angiotensin II receptor binding was determined using the adrenal glomerulosa assay. The ability to antagonize angiotensin-induced vasoconstriction was evaluated in the rabbit aorta test system.

Adrenal Glomerulosa Test System

Binding of $I^{125}$-angiotensin II to adrenal membranes was routinely carried out in 96-well filtration plates. Adrenal membranes were prepared from the capsular portion (glomerulosal layer attached) of rat adrenal glands by differential centrifugation. Briefly, capsules were homogenized in a solution containing sucrose, 250 mill; $MgCl_2$, 1 Mm; and tris, 5 Mm at pH 7.5 and 4° C. using a polytron at setting 5 for 20 seconds. The homogenate was stirred, gently, for 15 minutes at 4° C. and then centrifuged 10 minutes, at 1000 x g, 4° C. The supernatant was centrifuged 30 minutes, at 30,000 x g, 4° C. and the resulting pellet resuspended in 50 Mm tris. Membrane preparations were stored in aliquots at −70° C. until used. Binding of $I^{125}$-angiotensin II to adrenal membranes was performed at room temperature for 90 minutes in 96-well plates containing a hydrophilic polyvinylidene fluoride membrane (0.45 μm, millipore-GV multiscreen). Each 250 μl incubate contained the following (final concentration): tris, 50 Mm; NaCl, 120 mM; $MgCl_2$, 5 mM; dithiothrietol 1 Mm; bovine serum albumin, 0.05%; $I^{125}$-angiotensin II, 0.1 nM; and adrenal membrane protein, 8-15 pg. Antagonists were added in concentrations from 10 nM to 100 μM. Non-specific binding was measured in the presence of 0.1 μM Sar$_1$, Ile$_8$ angiotensin II. Binding was terminated by vacuum filtration. Receptor-ligand complex trapped on filters was washed 3 times with 300 μl ice-cold wash solution (tris, 50 MM; NaCl, 120 MM; $MgCl_2$, 5 mM; dithiothrietol, 1 mill). Filter discs were dried, punched out and counted in a gamma counter at 52% efficiency. Specific binding represented 96% of total binding (approximately 150 fmol angiotensin II/mg protein). Data are expressed as the percent inhibition of $I^{125}$ angiotensin binding at $10^{-5}$ m of antagonist.

Rabbit Aorta Test System

New Zealand white rabbits (Hazelton, 2-3 kg) were sacrificed by cervical dislocation and the thoracic aortas were removed and cleaned of excess fat and connective tissue. Rings of tissue (3 mm wide) were mounted in 10 ml tissue baths between 2 L-shaped stainless steel hooks. The lower hook was attached to a stationary rod and the upper hook to a force displacement transducer (Grass model FT.03). The bath chambers were maintained at 370C, aerated with 95% $O_2$/5% $CO_2$, and contained physiological solution of the following composition (mM): NaCl, 117; glucose, 5.6; $NaH_2PO_4$, 1.0; $MgSO_4$, 0.7; KCl, 5.2; $CaCl_2$, 1.8; $NaHCO_3$, 26; and phentolamine HCl, 0.003.

Rings were equilibrated for 1 hour with 2 g of tension. During the equilibration period, the tissues were washed by overflow every 15 minutes. Rings were then exposed to $10^{-8}$ M angiotensin II (AII) and were allowed to contract until a steady state was reached. Tissues were then washed every 15 minutes for 1 hour. This was repeated every hour until the AII response stabilized. A cumulative concentration-response curve to AII ($10^{-10}$ to $10^{-7}$ M) was then obtained. At the conclusion of the concentration-response curve, tissues were washed every 2 minutes until baseline tension was reached, then every 15 minutes for 30 minutes. Compounds were added in a volume of 10 μl DMSO and allowed to incubate for 30 minutes before repeating the concentration-response curve to AII. Contractions to AII were expressed as a percent of the maximum contraction obtained in the control curve (the first AII concentration-response curve). $EC_{50}$'s (concentration that contracted the tissues to ½ the control maximum) for each curve were calculated using a 4 parameter logistics model (NonLin, SAS institute). Potency data for each compound tested are expressed in Table 1 as the $pA_2$ (defined as $-\log K_B$, where $K_B$=(molar concentration of antagonist]/[($EC_{50}$ AII with antagonist-/$EC_{50}$ AII without antagonist)-1]).

TABLE 1

| Example | Adrenal Glomerulosa (% Inhibition of Binding) | Rabbit Aorta (pA₂) |
|---|---|---|
| 5 | 39 | 5.48 |
| 9 | 25 | 4.74 |
| 10 | 57 | 5.63 |
| 12 | 44 | 5.60 |
| 14 | 2 | 4.26 |
| 15 | 5 | 4.12 |
| 18 | 3 | 3.10 |
| 26 | 57 | 4.99 |
| 27 | 64 | 6.85 |
| 28 | 10 | 5.46 |
| 29 | 40 | 4.59 |
| 30 | 66 | 6.96 |
| 31 | 70 | 5.51 |
| 32 | 54 | 4.67 |
| 33 | 42 | 6.20 |
| 34 | 31 | 5.72 |
| 35 | 36 | 5.58 |
| 36 | 5 | 4.93 |
| 37 | 0 | 5.80 |
| 38 | 30 | 5.78 |
| 39 | 44 | 6.18 |
| 40 | 9 | 5.79 |
| 41 | 30 | 6.19 |
| 42 | 58 | 6.48 |
| 43 | 0 | 6.02 |
| 44 | 67 | 5.40 |
| 45 | 0 | 5.38 |
| 46 | 39 | 4.36 |
| 47 | 39 | 5.30 |
| 48 | 61 | 4.92 |
| 49 | 9 | 4.39 |
| 50 | 42 | 6.07 |
| 51 | 80 | 5.57 |
| 52 | 44 | 5.08 |
| 53 | 42 | 5.22 |
| 54 | 40 | 4.86 |
| 55 | 13 | 5.90 |
| 56 | 75 | 5.98 |
| 57 | 77 | 5.58 |
| 58 | 69 | 5.37 |
| 59 | 67 | 5.51 |
| 60 | 15 | 5.08 |
| 76 | 35 | 5.90 |
| 77 | 36 | 5.26 |
| 78 | 21 | 5.10 |
| 79 | 18 | 4.96 |
| 81 | 41 | |
| 82 | 62 | |
| 83 | 53 | 5.41 |
| 84 | 77 | 5.64 |
| 85 | 0 | 4.80 |
| 86 | 57 | 5.49 |
| 87 | 7 | 4.63 |
| 88 | 22 | |
| 89 | 54 | 4.41 |
| 94 | 58 | 5.78 |
| 96 | 59 | 6.43 |
| 97 | | 6.62 |

The term "pharmaceutically effective amount", as used herein, represents an amount of a compound of the invention which is capable of blocking angiotensin II receptors in mammals. The particular dose of compound administered according to this invention will, of course, be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

The compounds of Formula I are preferably formulated prior to administration. Therefore, yet another embodiment of the present invention is a pharmaceutical formulation comprising a compound of Formula I and one or more pharmaceutically acceptable carriers, diluents or excipients therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| α-Hexyl-4-[3-hydroxy-2-(tetrazol-5-yl)benzoyl]amino-1H-imidazole-1-acetic acid | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
| --- | --- |
| α-Hexyl-4-[3-hydroxymethyl-2-(tetrazol-5-yl)benzoyl]amino-1H-imidazole-1-acetic acid | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components.

|  | Weight % |
| --- | --- |
| α-Hexyl-4-[3-hydroxy-2-(tetrazol-5-ylmethyl)benzoyl]amino-1H-imidazole-1-acetc acid | 0.25 |
| ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| α-Hexyl-4-[3-hydroxy-2-(tetrazol-5-yl)]-1H-imidazole-1-acetic acid | 60 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| α-Hexyl-4-[(3-methylsulfonylamino-2-(tetrazol-5-yl)benzoyl]amino-1H-imidazole-1-acetic acid | 80 mg |
| --- | --- |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| β-Hexyl-4-[3-hydroxy-2-(tetrazol-5-yl)benzoyl]amino-1H-imidazole-1-propionic acid | 225 mg |
| --- | --- |
| saturated fatty acid glycerides | 2,000 mg |

-continued

| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medication per 5 ml dose are made as follows:

| α-Hexyl-4-[3-hydroxy-2-(tetrazol-5-yl)benzoyl]phenylacetic acid | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| α-Hexyl-4-[2-carboxy-3-hydroxybenzoyl)-amino]-1H-imidazole-1-acetic acid monohydrate | 250 mg |
| isotonic saline | 1000 ml |

The solution of the above ingredients is administered intravenously at a rate of 1 ml per minute to a subject in need of treatment.

We claim:

1. A compound of the formula

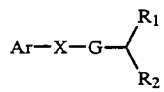

or a pharmaceutically acceptable salt or solvate thereof where G is

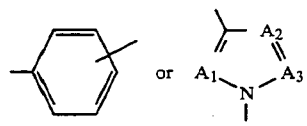

Ar is

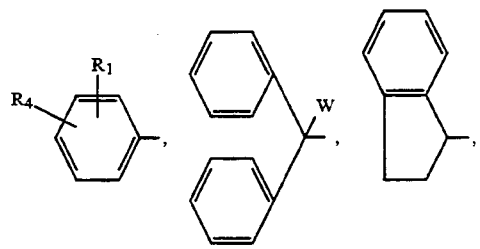

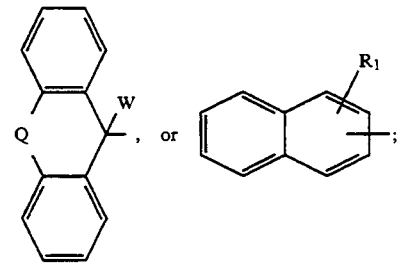

each of $A_1$, $A_2$, and $A_3$ is independently N or CH;
X is —O—, —CONH—, —NHCO—, —CH$_2$CONH—, —O—, —NH—, —CH$_2$—or a bond;
each $R_1$ is independently —(CH$_2$)$_n$R$_3$;
$R_2$ is $C_4$–$C_7$ straight chain alkyl;
each $R_3$ is independently —OH, —COOH, or 5-tetrazolyl;
each n is independently 0, 1, 2, 3, or 4,
$R_4$ is H, OH, halo, nitro, methyl, amino, acetamido, or methanesulfonamido;
Q is a bond or —O—; and
W is H, methyl, ethyl, or hydroxy,
provided that $A_2$ is not N when $A_1$ and $A_3$ are each CH and $R_1$ is —COOH or 5-tetrazolyl;
provided that if G is not imidazolyl or tetrazolyl, at least one $R_3$ is 5-tetrazolyl.

2. A compound of the formula

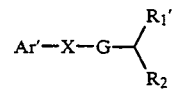

where G is

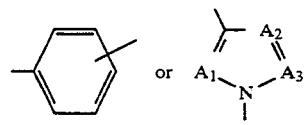

Ar' is

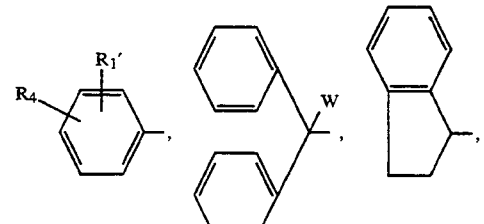

-continued

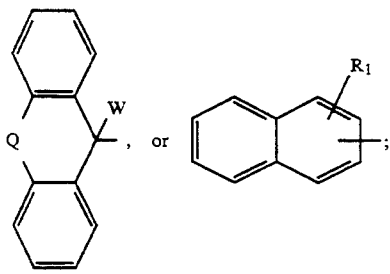

each of $A_1$, $A_2$, and $A_3$ is independently N or CH;
X is —CO—, —CONH—, —NHCO—, —CH$_2$CONH—, —O—, —NH—, —CH$_2$— or a bond;
each $R_1'$ is independently —(CH$_2$)$_n$R$_3'$;
$R_2$ is $C_4$-$C_7$ straight chain alkyl;
each $R_3'$ is independently —OH, —COOH, 5-tetrazolyl, —COO(C$_1$-C$_4$ alkyl), or —CN;
each n is independently 0, 1, 2, 3, or 4;
$R_4$ is H, OH, halo, nitro, methyl, amino, acetamido, or methanesulfonamide;
Q is a bond or —O—;
W is H, methyl, ethyl, or hydroxy; provided at least one $R_3'$ is —COO(C$_1$-C$_4$ alkyl) or —CN; provided that G is imidazolyl or tetrazolyl.

3. A compound of claim 2 wherein $A_2$ is N and $A_1$ and $A_3$ are each CH.

4. A compound of claim 3 of the formula

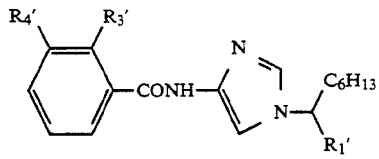

wherein
$R_4'$ is H or OH.

5. The compound of claim 4 which is α-hexyl-4-[(2-carboxy-3-hydroxybenzoyl)amino]-1H-imidazole-1-acetic acid ethyl ester.

6. The compound of claim 4 which is β-hexyl-4-[(2-carboxy-3-hydroxybenzoyl)amino]-1H-imidazole-1-propanoic acid methyl ester.

7. The compound of claim 4 which is α-hexyl-4-{[2-(tetrazol-5-yl)benzoyl]amino}-1H-imidazole-1-acetic acid ethyl ester.

8. A method of blocking angiotensin II receptors in mammals which comprises administering to a mammal requiring inhibition of the action of angiotensin II at its receptors a pharmaceutical amount of a compound of claim 1.

9. A method of treating hypertension in a mammal comprising administering to a mammal in need of treatment from hypertension an antihypertensive amount of a compound of claim 1.

10. A pharmaceutical formulation comprising a compound of claim 1 and one or more pharmaceutically acceptable carriers, diluents, or excipients therefor.

* * * * *

UNITED STATES PATENT AND TRADEMARK OFFICE
CERTIFICATE OF CORRECTION

PATENT NO. : 5,312,936
DATED : May 17, 1994
INVENTOR(S) : Sherryl L. Lifer, et al It is certified that error appears in the above-indentified patent and that said Letters Patent is hereby corrected as shown below:

Column 31, Line 63: -- ; -- should appear after the structure.

Column 32, Line 25: "-O-" should be -- -CO- --.

Column 32, Line 31: "4" should be -- 4; --.

Column 32, Line 35: "hydroxy" should be -- hydroxy; --.

Column 33, Line 24: "methanesulfonamide" should be -- methanesulfonamido --

Signed and Sealed this

Sixth Day of September, 1994

Attest:

BRUCE LEHMAN

Attesting Officer

Commissioner of Patents and Trademarks